United States Patent [19]

Lukenbach

[11] Patent Number: 5,292,943
[45] Date of Patent: Mar. 8, 1994

[54] METHOD FOR THE PREPARATION OF LOW ODOR 2,3-DIMERCAPTOSUCCINIC ACID

[75] Inventor: Elvin R. Lukenbach, Flemington, N.J.

[73] Assignee: McNeil - PPC, Inc., Milltown, N.J.

[21] Appl. No.: 824,640

[22] Filed: Jan. 23, 1992

[51] Int. Cl.$^5$ ............................................. C07C 323/00
[52] U.S. Cl. .................................................... 562/594
[58] Field of Search ........................................ 562/594

[56] References Cited

U.S. PATENT DOCUMENTS 4,550,193 10/1985 Lindemann ........................ 560/147

OTHER PUBLICATIONS

CA:104(21)185992g 2,3-Dimercaptosuccinic acid and its lower alkyl esters; Lindemann, Martin K. O.; Lukenbach, Elvin R.
CA:72(11)54600a (+)-2,3-Dimercaptosuccinic acid.

Primary Examiner—José G. Dees
Assistant Examiner—Joseph M. Conrad, III

[57] ABSTRACT

A method for producing low odor meso-2,3-dimercaptosuccinic acid is provided whereby a meso-2,3-dimercaptosuccinic acid substrate is washed with an aqueous wash medium and subsequently dried, preferably at a temperature of less than 40° C. and a low odor meso-2,3-dimercaptosuccinic acid is also provided by this invention.

7 Claims, No Drawings

METHOD FOR THE PREPARATION OF LOW ODOR 2,3-DIMERCAPTOSUCCINIC ACID

FIELD OF THE INVENTION

This invention relates to a process to prepare a low odor 2,3-dimercaptosuccinic acid. More particularly, a meso 2,3-dimercaptosuccinic acid substrate, generally in crude or crystalline form, is washed with an aqueous wash medium and preferably dried at a temperature of less than about 40° C.

BACKGROUND OF THE INVENTION

Meso 2,3-dimercaptosuccinic acid (DMSA) is a compound analogous to 2,3-dimercaptopropanol (BAL). In contrast to BAL however, DMSA is less toxic, has greater water solubility, limited lipid solubility, and is effective when given orally. (*Fund. Appl. Tox* 11:715–722 (1988)).

Methods to prepare DMSA are known. For example, acetylene dicarboxylic acid can be reacted with thiolacetic acid or sodium thiosulfate to produce an intermediate which can be hydrolyzed to yield crude DMSA. See e.g., U.S. Pat. No. 4,550,193. Crystalline DMSA is typically obtained by crystallizing crude DMSA from, an alcohol, e.g., methanol and ethanol.

2,3-Dimercaptosuccinic acid exists in two forms, the meso form and the DL form. Because meso-DMSA is easier to synthesize and purify, it is more readily available, and has been used in most published investigations and is the subject of this patent application. Meso-DMSA is sparingly soluble and must be titrated to approximately pH 5.5 to go into solution, or dissolved in 5% $NaHCO_3$. The DL form on the other hand, is readily soluble in distilled water. (*Ann. Rev. Pharmacol. Toxicol.* 23:193–125 (1983)). As used in this invention, the abbreviation "DMSA", unless otherwise stated, refers to the meso forms. DMSA is available from a variety of biochemical specialty firms.

DMSA was originally introduced by Friedheim and DaSilva in 1954 to promote uptake of antimony during schistosomiasis therapy (*J. Pharm. Exp. Therap.* 246:84 (1988)), and was first recognized as an antidote for heavy metal toxicity by Liang et al. in 1957 (*Acta Physiol. Sin.* 21:24–32 (1957)). Since then, DMSA has been shown to remove toxic forms of lead, mercury and arsenic from the body via urinary excretion, presumably by forming water-soluble metal complexes or chelates (*Anal. Biochem.* 160:217–226 (1987)).

DMSA has been shown to have variable success as an antidote for other toxicities. DMSA was reported to be effective at reducing the concentration of aluminum in the liver, spleen and kidney (*Res. Com. Chem. Pathol. Pharm.* 53:93–104 (1986)), reducing the concentration of cobalt in the liver, brain, heart and blood (*Arch. Toxicol.* 58:278–281 (1986)), and as an antagonist for acute oral cadmium chloride intoxication by increasing the urinary elimination of cadmium (*Tox. Appl. Pharm.* 66:361–367 (1982)). DMSA however, did not increase urinary and fecal excretion of cobalt (*Arch. Toxicol.* 58:278–281 (1986)), and showed lower efficacy than other chelating agents as an antidote for zinc poisoning (*Arch. Toxicol.* 61:321–323 (1988)). (See *Ann. Rev. Pharm. Toxicol.* 23:193–215 (183) for a review of the success and failure of DMSA in treating toxicities).

DMSA has also been labeled with $^{99}Tc$ for use in renal scanning (*J. Nucl. Med.* 16:28–32 (1973), tumor detection (*Clin. Otalary* 12:405–411 (1987); *Clin. Nucl. Med.* 13:159–165 (1988)) and for imaging myocardial infarcts (*Clin. Nucl. Med.* 12:514–518 (1987)).

Recently, administration of DMSA has been used as a treatment for pediatric lead poisoning. Associated with DMSA, is a strong objectionable sulfidic odor. An objectionable odor is generally undesirable, particularly with a product having pharmaceutical utility and oral activity such as DMSA. For compounds administered orally, some degree of voluntary compliance is required and an objectionable odor can negatively impact on patient compliance particularly in pediatric applications.

It is therefore an object of the present invention to provide a low odor DMSA suitable for adult and pediatric oral administration.

SUMMARY OF INVENTION

This invention provides a novel method to prepare low odor DMSA comprising washing a meso-2,3-dimercaptosuccinic acid substrate, e.g. crystalline DMSA, at least twice with an aqueous wash medium, preferably substantially pure water, and drying the washed meso-2,3-dimercaptosuccinic acid substrate. In another embodiment of this invention, a low odor DMSA is prepared by washing a meso-2,3-dimercaptosuccinic acid substrate, e.g. crystalline DMSA, at least once with an aqueous wash medium, preferably substantially pure water, and drying the washed meso-2,3-dimercaptosuccinic acid substrate at a temperature of about 40° C. or less. Applicant has recognized that by subjecting a DMSA substrate with an objectionable odor to the method of this invention, a low odor DMSA is produced which is more desirable particularly for oral pediatric therapies.

Further provided by this invention is a low odor meso-2,3-dimercaptosuccinic acid obtained by washing a meso-2,3-dimercaptosuccinic acid substrate at least twice with an aqueous wash medium and drying the washed meso-2,3-dimercaptosuccinic acid substrate In another embodiment of this invention, there is provided a low odor meso-2,3-dimercaptosuccinic acid obtained by washing a meso-2,3-dimercaptosuccinic acid substrate at least once with an aqueous wash medium and drying the washed meso-2,3-dimercaptosuccinic acid substrate at a temperature of about 40° C. or less.

Further provided by this invention is a method of low odor administration of meso-2,3-dimercaptosuccinic acid comprising administering to a patient a prescribed effective dosage amount of a low odor meso-2,3-dimercaptosuccinic acid obtained by washing a meso-2,3-dimercaptosuccinic acid substrate at least twice with an aqueous wash medium; and drying the washed meso-2,3-dimercaptosuccinic acid substrate

DETAILED DESCRIPTION OF THE INVENTION

Meso-2,3-dimercaptosuccinic acid produced by methods known to those in the art, such as methods described in U.S. Pat. No. 4,550,193, has an objectionable sulfidic odor and is a suitable substrate for use in this invention. For example, crude DMSA (a precipitated powder), i.e., the reaction product of any method to prepare DMSA prior to purification steps, can be used so long as the final step of dissolution is carried out in an aqueous alkali solution followed by precipitation with an appropriate aqueous acid reagent. Also crystalline DMSA, as distinguished from precipitated powder, i.e., crude DMSA which has been purified to a higher percentage of DMSA by known techniques such as dioxane treatment and recrystallization with an alcohol may be useful in the invention. Typically, crystalline DMSA is available at about 98% purity. A high purity crystalline DMSA substrate is preferred for use in the invention where the low odor product is intended for mammalian consumption.

The objectionable sulfidic odor in the DMSA substrate of this invention is believed to be caused by mercaptan impurities or decomposition products resulting from contact with organics during preparation/crystallization and/or subsequent drying conditions. The term "low odor" as used herein refers to DMSA with no odor or a lesser sulfidic odor than a DMSA substrate untreated by the process of this invention.

In one embodiment of the invention, the DMSA substrate is then washed at least twice with an aqueous wash medium to produce a lower odor DMSA than the substrate. Preferably, the wash medium contains less than about 10% by weight organics, such as alcohols. Most preferably, the aqueous wash medium is substantially pure water. The presence of excess organics, such as ethanol, in the wash medium contribute to an increased odor associated with the product. The washing preferably takes place under mixing conditions or other modes of dispersion to promote contact of wash medium with the DMSA.

The DMSA is washed for a time sufficient to yield a product with a lesser sulfidic odor than the substrate DMSA. Typically, washing times on the order of five minutes are sufficient for a small quantity of product.

Following the washing described herein, the DMSA is dried. Preferably, the washed DMSA is dried at about 40° C. or less and most preferably, at about 30° C. or less. The upper limit on drying temperature is governed by an undesirable increase in odor associated with a product dried at higher temperatures. The lower limit on drying temperature is governed by convenience and economics. Drying temperatures will also vary depending on the equipment used, e.g., freeze drying or vacuum drying would provide different drying temperatures as would be known to those skilled in the art.

In another embodiment of this invention, the DMSA substrate is washed at least once with an aqueous wash medium to produce a lower odor DMSA than the substrate when dried in accordance with the invention. Preferably, the wash medium contains less than 2% by weight organics. Most preferably, the aqueous wash medium is substantially pure water. The washing preferably takes place under mixing conditions or other modes of dispersion to promote contact of wash medium with the DMSA.

The DMSA is washed for a time sufficient to yield a product with a lesser sulfidic odor than the substrate DMSA after drying in accordance with this invention. Typically, washing times on the order of five minutes are sufficient for a small quantity of product.

The washed DMSA is then dried at a temperature of about 40° C. or less and preferably, at about 30° C. or less. The upper limit on drying temperature is governed by an undesirable increase in odor associated with a product dried at higher temperatures. The lower limit on drying temperature is governed by drying methods, convenience and economics.

The washed DMSA may be filtered prior to drying and dried under vacuum where desired to facilitate the drying process.

Further provided by this invention is a low odor meso-2,3-dimercaptosuccinic acid obtained by washing a meso-2,3-dimercaptosuccinic acid substrate at least twice with an aqueous wash medium and drying the washed meso-2,3-dimercaptosuccinic acid substrate at a temperature of about 40° C. or less as described herein. In another embodiment of this invention, a low odor meso-2,3-dimercaptosuccinic acid is obtained by washing a meso-2,3-dimercaptosuccinic acid substrate at least once with an aqueous wash medium and drying the washed meso-2,3-dimercaptosuccinic acid substrate at a temperature of about 40° C. or less as described herein.

EXAMPLES

Material 206.85 gm meso-DMSA

Procedure

As a control, approximately 7 gm DMSA was placed in a covered 2 oz. glass jar.

Example 1 ($1 \times H_2O$ wash):

The remainder, about 200 g of DMSA, was suspended in 200 ml distilled water, stirred for five minutes and suction filtered. This collected solid was treated as described below.

In this example, a 50 gm sample of the starting filtrate received no further treatment. This sample was divided equally into three 2 oz. glass jars and dried as follows:
1) at 50° C. under 20" Hg vacuum;
2) at 25° C. under 20" Hg vacuum; and
3) air dried at ambient temperature and pressure.

Example 2 ($2 \times H_2O$ wash):

The remaining collected solid from Example 1 was suspended in deionized water, stirred five minutes and filtered by suction as described in Example 1. A 50 gm sample of this collected solid was divided into three 2 oz. glass jars and dried as described in Example 1.

Comparison A ($2 \times H_2$wash/EtOH wash)

The remaining collected solid from Example 2, now washed with water twice by the treatment of Examples 1 and 2, was suspended in 200 ml 100% ethanol, stirred five minutes and suction filtered. A 50 gm sample of this collected solid was divided into three 2 oz. glass jars and dried as described in Example 1.

Example 3 ($2 \times H_2$wash/EtOH wash/$H_2O$ wash)

The remaining collected solid from Comparison A, now washed two times with water and once with ethanol as described in Examples 1, 2 and Comparison A, was again suspended in deionized water, stirred five minutes and suction filtered as described in Example 1. The collected solid was divided into three 2 oz. glass jars and dried as described in Example 1.

All twelve samples were maintained in their drying stations until dried and stirred at least once. All samples, when judged dry were closed and set aside until all samples were dry. When all were dry, odor evaluation was conducted.

Odor evaluation was conducted by the same individual. The results of the odor evaluation are summarized below in Table I.

TABLE I

| | Example 1 | Example 2 | Comparison A | Example 3 |
|---|---|---|---|---|
| 50° C. vac dry | SO | VLO | VSO | SO |
| 25° C. vac dry | NO | NO | SO | NO |
| air dry | NO | NO | SO | NO |

*Samples were given the following ratings:
(1) "NO" substantially no odor;
(2) "VLO" very little odor;
(3) "SO" a strong odor, substantially the same as the control; and
(4) "VSO" a very strong odor, greater than the control.

Application of the compositions and processes of the present invention for medical and pharmaceutical uses can be accomplished by any chemical, clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A method of preparing low odor meso-2,3-dimercaptosuccinic acid comprising:
    washing a meso-2,3-dimercaptosuccinic acid substrate at least twice with an aqueous wash medium containing less than about 10% by weight alcohol; and
    drying the washed meso-2,3-dimercaptosuccinic acid substrate.

2. The method of claim 1 wherein the washing is conducted under mixing conditions.

3. The method of claim 1 wherein the washed meso-2,3-dimercaptosuccinic acid substrate is dried at a temperature of about 40° C. or less.

4. The method of claim 1 wherein the washed meso-2,3-dimercaptosuccinic acid substrate is dried at a temperature of about 30° C. or less.

5. A method of preparing low odor meso-2,3-dimercaptosuccinic acid comprising:
    washing a meso-2,3-dimercaptosuccinic acid substrate at least with an aqueous wash medium containing less than about 10%, by weight alcohol; and
    drying the washed meso-2,3-dimercaptosuccinic acid substrate at a temperature of about 40° C. or less.

6. The method of claim 5 wherein the washing is conducted under mixing conditions.

7. The method of claim wherein the washed meso-2,3-dimercaptosuccinic acid substrate is dried at a temperature of about 30° C. or less.

* * * * *

UNITED STATES PATENT AND TRADEMARK OFFICE
CERTIFICATE OF CORRECTION

PATENT NO. : 5,292,943
DATED : March 8, 1994
INVENTOR(S) : Lukenbach

It is certified that error appears in the above-identified patent and that said Letters Patent is hereby corrected as shown below:

Column 6, Claim 5, line 17, after "least" should be -- once --.

Column 6, Claim 7, line 23, after "claim" should be -- 5 --.

Signed and Sealed this

Eighth Day of November, 1994

Attest:

BRUCE LEHMAN

Attesting Officer

Commissioner of Patents and Trademarks